(12) United States Patent
Clarot et al.

(10) Patent No.: US 7,439,269 B2
(45) Date of Patent: Oct. 21, 2008

(54) COMPOSITION AND METHOD FOR MOISTURIZING NASAL TISSUE

(75) Inventors: Tim Clarot, Phoenix, AZ (US); Charles Hensley, Woodland Hills, CA (US)

(73) Assignee: Matrixx Initiatives, Inc., Phoenix, AZ (US)

( * ) Notice: Subject to any disclaimer, the term of this patent is extended or adjusted under 35 U.S.C. 154(b) by 345 days.

(21) Appl. No.: 11/109,128

(22) Filed: Apr. 18, 2005

(65) Prior Publication Data

US 2005/0180924 A1     Aug. 18, 2005

Related U.S. Application Data

(60) Division of application No. 10/243,637, filed on Sep. 13, 2002, now abandoned, which is a continuation-in-part of application No. 09/388,816, filed on Sep. 1, 1999, now Pat. No. 6,673,835, which is a continuation-in-part of application No. 09/145,042, filed on Sep. 1, 1998, now Pat. No. 6,080,783, application No. 11/109, 128, and a continuation-in-part of application No. 09/956,744, filed on Sep. 12, 2001, which is a continuation of application No. 09/145,042, filed on Sep. 1, 1998, now Pat. No. 6,080,783.

(51) Int. Cl.
  *A61K 31/047*     (2006.01)
  *A61K 31/355*     (2006.01)
  *A61K 9/00*       (2006.01)
  *A61K 9/10*       (2006.01)
  *A61K 9/127*      (2006.01)
  *A61P 17/16*      (2006.01)
  *A61P 39/00*      (2006.01)

(52) U.S. Cl. .............. 514/738; 514/458; 514/944; 514/964; 424/434; 424/450; 424/484; 424/744

(58) Field of Classification Search ................ 514/458, 514/738, 944, 964; 424/434, 450, 484
See application file for complete search history.

(56) References Cited

U.S. PATENT DOCUMENTS 5,200,393 A * 4/1993 Weiner ........................ 514/3
5,993,850 A * 11/1999 Sankaram et al. ........... 424/450

FOREIGN PATENT DOCUMENTS

WO         99/38492        *  8/1999

OTHER PUBLICATIONS

Hirt, M. et al., "Zinc nasal gel for the treatment of common cold symptoms: a double-blind, placebo-controlled trial," Oct. 2000, pp. 778-780 and 782.*
Martindale The Extra Pharmacopoeia, 30th edition, The Pharmaceutical Press, London, 1993, pp. 1374-1375.*
Flick, E.W. Cosmetics Additives An Industrial Guide. Noyes Publications, Park Ridge (NJ), 1991, pp. 76 and 155.*

* cited by examiner

*Primary Examiner*—John Pak
(74) *Attorney, Agent, or Firm*—Snell & Wilmer L.L.P.

(57) ABSTRACT

An improved composition and method for moisturizing a nasal membrane are disclosed. The composition includes a viscous carrier and one or more moisturizing agents disposed with the carrier. The composition is applied to a portion of a nasal membrane using a spray, a swab applicator, or a similar application device.

6 Claims, No Drawings

COMPOSITION AND METHOD FOR MOISTURIZING NASAL TISSUE

CROSS-REFERENCE TO RELATED APPLICATIONS

This application is divisional of U.S. application Ser. No. 10/243,637, entitled "COMPOSITION AND METHOD FOR MOISTURIZING NASAL TISSUE," filed Sep. 13, 2002, now abandoned, which is a continuation-in-part of U.S. patent application Ser. No. 09/388,816, entitled "METHOD AND COMPOSITION FOR DELIVERING ZINC TO THE NASAL MEMBRANE" and filed on Sep. 1, 1999, now U.S. Pat. No. 6,673,835, which is a continuation-in-part of U.S. patent application Ser. No. 09/145,042, entitled "METHOD AND COMPOSITION FOR DELIVERING ZINC TO THE NASAL MEMBRANE" and filed on Sep. 1, 1998, now U.S. Pat. No. 6,080,783; and is a continuation-in-part of U.S. patent application Ser. No. 09/956,744, entitled "METHOD AND COMPOSITION FOR DELIVERING ZINC TO THE NASAL MEMBRANE" and filed on Sep. 12, 2001; which is a continuation of U.S. patent application Ser. No. 09/145,042, entitled "METHOD AND COMPOSITION FOR DELIVERING ZINC TO THE NASAL MEMBRANE" and filed on Sep. 1, 1998, now U.S. Pat. No. 6,080,783.

TECHNICAL FIELD

The present invention generally relates to a method and composition for moisturizing nasal tissue.

BACKGROUND INFORMATION

Compounds suitable for moisturizing a nasal cavity or a portion of a nasal cavity are desirable for several reasons. For example, application of a moisturizer to the nasal cavity may facilitate and/or promote healthy function of the cavity, which in turn may reduce the duration of symptoms associated with, for example, a common cold or the flu, and which may reduce the likelihood of an infection in the nasal region.

In general, the nasal cavity performs several functions. The lower portion of the cavity includes the nasal epithelium, which is an essential part of the respiratory tract. The nasal epithelium is very vascular, which allows the epithelium to warm inspired air. The epithelium is also relatively moist, which allows it to moisten and cleanse inspired air. The cavity also includes a mucous membrane which lines the nasal cavity and traps fine particles such as dust, pollen and smoke.

Nasal epithelial cells play an important role in warding of both bacteria and viruses. The cells act as a chemical, mechanical and microbiological barrier to infection. Typically, small glands within the nose secrete mucus, onto the nasal epithelial cells to moisten a portion of the nasal membrane. The cilia, hair like structures implanted in the epithelium and the immune system's first line of defense, are the cells responsible for trapping dust and bacteria. When the nasal membrane becomes dry, the cilia's movement slows and bacteria are better able to enter the respiratory system. To effectively function, the epithelial cells must generally be healthy and moist.

Substances within air often act to irritate and dry out the nasal cavity. Sinusitis and allergens are two common conditions that affect the proper functioning of the nasal membrane. Sinusitis is an infection of any of the four groups of sinuses that prevents the proper drainage of mucous in the sinus passages. Sinusitis may stem from a cold or flu, allergies, pollution, injuries or various other conditions, which often result in a dry nasal passage.

Inhaled allergens, including dust, pollen, molds, animal dander, and grass may react with the mucous membrane. This reaction may result in a drying or irritation of the nasal cavity. These factors along with dry climates, changing seasons, and pollution can all lead to nasal cavity dryness which may cause cracking and bleeding of the nose as well as various other acute or chronic conditions. Accordingly, methods and compositions for moisturizing a nasal membrane are desired.

Presently, common treatment for nasal membrane dryness is either use of low-viscosity composition nasal sprays or use of a humidifier. Low-viscosity, over the counter nasal sprays generally remain in the nasal cavity only for a short period of time and therefore may be relatively ineffective at treating dry nasal cavities. A humidifier generally requires that the subject utilizing the humidifier remain proximate to the humidified air for a period of time and such use may therefore be problematic or undesirable in some instances. Accordingly, improved compositions, systems and methods for moisturizing the nasal membrane are desired.

SUMMARY OF THE INVENTION

The present invention provides improved methods and compositions for moisturizing the nasal membrane.

While the way in which the present invention addresses the disadvantages of the prior art will be discussed in greater detail below, in general, the present invention provides an effective nasal moisturizer that does not irritate nasal epithelium.

In accordance with one exemplary embodiment of the present invention, the nasal moisturizer is a composition that includes an active moisturizing ingredient within a viscous gel. The gel has a viscosity in the range of 2,500 to 40,000 centipoise, preferably in the range of 5,000 to 20,000 centipoise. The active ingredient may include any number of materials appropriate for moisturizing nasal tissue. In accordance with one aspect of this embodiment of the invention, the nasal moisturizer is configured to facilitate maintaining the composition within the nasal membrane for a period of time long enough to effectively moisturize the nasal membrane.

In accordance with another embodiment of the invention, a nasal moisturizer includes a gel and an encapsulated moisturizing agent. In accordance with one aspect of this embodiment, the gel includes purified water and glycerin. In accordance with another aspect of this embodiment of the invention, the moisturizing agent includes aloe barbadensis gel. In accordance with a further aspect of this embodiment, the composition includes a thickener.

In accordance with another embodiment of the invention, the composition includes a nasal moisturizing agent encapsulated within lipid or liposomal vesicles. In accordance with various aspects of this embodiment, lipid or liposomal vesicles are formed of unilamellar vesicles or multilamellar vesicles.

In accordance with another embodiment of the invention, a method of treating a dry nasal membrane includes applying a nasal moisturizing composition to the nasal cavity using a nasal spray, aerosol or swab applicator.

DETAILED DESCRIPTION OF EXEMPLARY EMBODIMENTS

The present invention provides an improved composition for relieving symptoms of a dry nasal membrane and a method of using the same. The invention is conveniently described herein in terms of a high viscosity nasal moisturizing compound that can be easily applied through use of a nasal or aerosol spray, swab applicator or the like. It should be appreciated that the functional composition may be realized by any number of combinations of the ingredients listed below. For example, the composition may vary in its viscosity level, which will allow the composition to be suitably configured for various intended applications.

The nasal moisturizing composition of the present invention generally includes a carrier and one or more active ingredients dispersed within the carrier. In accordance with various embodiments of the invention, the composition includes about 80-99.999 weight percent and preferably about 90-99.999 weight percent of a carrier. The carrier includes ingredients that are compatible with the nasal membrane and which form a composition having a viscosity high enough to maintain the composition in contact with the nasal membrane for an extended period of time. An exemplary carrier composition includes purified water, glycerin and a suitable thickening agent, and has a viscosity of about 2,500-40,000 centipoise and preferably about 5,000-20,000 centipoise, as measured using the Brookfield Syncho-Lectric Viscometer for the measurement of the apparent viscosity of newtonian and non-newtonian materials at low shear rates at given rotational speeds. The high viscosity carrier allows the composition to maintain contact with the nasal cavity without being drawn out by gravity or other forces which in turn allows active ingredient(s) within the carrier to remain proximate to or in contact with the nasal membrane.

In accordance with one exemplary embodiment of the invention the composition includes about 95-97 weight percent purified water and about 0.75-1.25 weight percent glycerin which are mixed together to form a composition as discussed in more detail below, the composition may also include a thickener to further increase the viscosity of the composition.

The active ingredients in the compositions of the present invention may be selected to perform a desired function. In accordance with various embodiments of the invention, the active ingredients include agents that act to moisturize the nasal tissue without irritating the nasal cavity. The active ingredients may include, but are not limited to, moisturizing agents such as, glycerin, aloe barbadensis gel, tocopherol and the like. In accordance with one exemplary embodiment of the invention the composition includes about 0.001-2.0 weight percent active ingredient, and preferably about 0.002 to 1.25 weight percent.

The composition may also include various optional ingredients such as additional thickeners, buffers, antibacterial agents and/or anti-microbial agents and/or preservatives to preserve and/or stabilize the formulations for manufacturing and storage. A buffer is used to maintain physiological pH. The composition may include any buffer that is capable of maintaining the desired pH. Exemplary buffers include, but are not limited to, sodium phosphate (monohydrate)/disodium phosphate (heptahydrate), sodium bicarbonate, and monobasic potassium phosphate/sodium hydroxide. A preservative maintains the sterility of the nasal moisturizer and may be used to extend the shelf life of the composition. Exemplary preservatives include, but are not limited to benzalkonium chloride, phenycarbinol and thimerosal. An antibacterial agent maintains the sterility of the composition and may also inhibit bacteria reproduction inside the nasal cavity. Exemplary antibacterial agents include, but are not limited to, hydrolyzed algin and chlorella vulgaris extract. An anti-microbial agent maintains the sterility of the composition, stabilizes the composition and may also kill pathogens inside the nasal cavity. Exemplary anti-microbial agents include, but are not limited to, chlorobutanol, sulfur dioxide, tetracycline, sorbic acid, ethanol, chlorohexidine, terconazole, nystatin, clotrimazole, and butoconazole.

The nasal moisturizing composition may also include any one or more of additional pharmaceutical and/or cosmetic agents. These agents may facilitate the preservation of the composition. Exemplary pharmaceutical or cosmetic agents include, for example, benzyl alcohol, disodium EDTA, hydroxylated lecithin, alkoxylated diester, polysorbate 80, polysorbate 65, and procaine hydrochloride.

One or more of the active ingredients may be encapsulated within lipid or liposomal vesicles to facilitate time-release dispersement of the active ingredients. This encapsulated composition allows for the active ingredient to be incorporated into the nasal tissue at a higher concentration than the active ingredient's water or lipid solubility, thereby allowing for increased absorption of the active ingredient into the nasal membrane.

As noted above, in accordance with various aspects of the invention, the nasal moisturizing composition includes a moisturizing agent. The moisturizing agent may be either a water soluble or lipid soluble composition that effectively moisturizes epithelial tissue. The moisturizing ingredient may also include a humectant. A humectant is a substance that promotes the retention and absorption of moisture from the air. Exemplary humectants include, but are not limited to glycerin, polyethylene glycol, polypropylene glycol, urea, sodium pyroglutamate, amino acids and the like. In accordance with one embodiment of the invention the humectant is glycerin.

In accordance with an alternative embodiment of the invention, the nasal moisturizing composition includes purified water, one or more thickeners and a moisturizing agent. The purified water is the solvent for the composition and acts to maintain the composition's proper viscosity level. The thickeners operates to increase the viscosity level of the composition to a level high enough to maintain the composition in contact with the nasal membrane for a period of time long enough to moisturize the nasal tissue. The thickener may include, but is not limited to glycerin and hydroxyethylcellulose.

In further accordance with this embodiment, the composition includes one or more active ingredients dispersed within the carrier. In accordance with various aspects of this embodiment, the active ingredients act to moisturize the nasal tissue without irritating the nasal cavity. The active moisturizing ingredients may include, but are not limited to moisturizing agents such as, glycerin, aloe barbadensis gel, tocopherol and the like.

In accordance with another aspect of this exemplary embodiment of the invention, the moisturizing composition includes one or more time release active ingredients dispersed throughout the composition. In accordance with one aspect of the invention, the time release ingredient is encapsulated within lipid or liposomal vesicles. The lipid or liposomal vesicles are formed, for example, of unilamellar vesicles or multilamellar vesicles as described in U.S. Pat. No. 6,048,545. In accordance with another aspect of this embodiment, the moisturizing agents may include moisturizing agents such as, glycerin, aloe barbadensis gel, tocopherol and the like.

In accordance with another embodiment of the invention, the nasal moisturizing composition comprises:

a gel including purified water and glycerin, wherein the purified water is present in an amount that is at least 80 weight percent, based on the total weight of the composition, and the glycerin is present in an amount from about 0.001 to 2.25 weight percent, based on the total weight of the composition;

about 0.5 to 2.0 weight percent hydrophilic thickener; and about 0.001 to 2.25 weight percent time-release moisturizing agent wherein the moisturizing agent is encapsulated.

Each of the embodiments and each of the compositions are suitable for application to the nasal membrane using a swab applicator, a spray applicator or other device. The swab applicator is a device that fully encapsulates both the composition and the applicator. Each swab applicator device includes a desired amount of the composition, for example, approximately one ounce of composition and a sterile cotton swab applicator encased and sealed in a plastic tube. In this case each device has approximately enough composition for one application.

The example provided below illustrates an exemplary nasal moisturizing compound of the present invention. The example is provided for illustration purposes only. This invention is not limited to the specific example provided herein.

EXAMPLE 1

| Components | Weight Percent Range | Exemplary Value |
|---|---|---|
| Purified Water | 95-100.00 | 95.522% |
| Sodium Phosphate | 1.500-3.000 | 1.5% |
| Hydroxyethylcellulose | 1.000-1.500 | 1.0% |
| Disodium Phosphate | 1.000-1.500 | 1.0% |
| Glycerin | 0.750-1.250 | 0.75% |
| alkoxylated Diester | 0.001-0.500 | 0.001% |
| Aloe Barbadensis Gel | 0.001-0.250 | 0.001% |
| Hydrolyzed Algin | 0.001-0.060 | 0.001% |
| *Chlorella Vulgaris* Extract | 0.001-0.060 | 0.001% |
| Sea Water | 0.001-1.000 | 0.001% |
| Benzalkonium Chloride | 0.010-0.100 | 0.01% |
| Benzyl Alcohol | 0.200-0.500 | 0.20% |
| Disodium EDTA | 0.010-0.100 | 0.01% |
| Hydroxylated Lecithin | 0.001-1.000 | 0.001% |
| Tocopherol | 0.001-0.100 | 0.001% |
| Polysorbate 80 | 0.001-0.100 | 0.001% |

The solution is prepared by admixing the various components together.

The present invention has been described above with reference to exemplary embodiments. Those skilled in the art having read this disclosure will recognize that changes and modifications may be made to the embodiments without departing from the scope of the invention. For instance, the present invention has been described in connection with particular active moisturizing agents; however, various other active ingredients may suitably be used with the moisturizing compounds of the present invention. These and other changes or modifications are intended to be included within the scope of the present invention, as expressed in the following claims.

We claim:

1. A composition for moisturizing a nasal membrane comprising:

a gel including purified water and glycerin, wherein the purified water is present in an amount that is at least 80 weight percent, based on the total weight of the composition, and the glycerin is present in an amount from about 0.001 to 2.25 weight percent, based on the total weight of the composition;

about 0.5 to 2.0 weight percent hydrophilic thickener; and about 0.001 to 2.25 weight percent time-release moisturizing agent wherein the moisturizing agent is encapsulated.

2. The composition of claim 1, further comprising a humectant.

3. The composition of claim 1, wherein said hydrophilic thickener comprises hydroxyethylcellulose.

4. The composition of claim 1, wherein the moisturizing agent in said time-release moisturizing agent is selected from the group consisting of glycerin, aloe barbadensis gel and tocopherol.

5. The composition of claim 1, further comprising one or more material selected from the group consisting of hydroxyethylcellulose, hydrolyzed algin, chlorella vulgaris extract, sea water, sodium phosphate (monohydrate), disodium phosphate (heptahydrate), alkoxylated diester, disodium EDTA, hydroxylated lecithin, polysorbate 80, benzyl alcohol, and benzalkonium chloride.

6. A system for applying a moisturizing composition onto a portion of a nasal cavity comprising the composition of claim 1 and an applicator.

* * * * *